US010088537B2

(12) United States Patent
Pendse et al.

(10) Patent No.: US 10,088,537 B2
(45) Date of Patent: Oct. 2, 2018

(54) METHOD AND APPARATUS FOR SAR FOCUSING WITH AN ARRAY OF RF TRANSMITTERS

(71) Applicant: The Board of Trustees of the Leland Stanford Junior University, Palo Alto, CA (US)

(72) Inventors: Mihir R. Pendse, Fremont, CA (US); Brian K. Rutt, Stanford, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 637 days.

(21) Appl. No.: 14/711,484

(22) Filed: May 13, 2015

(65) Prior Publication Data

US 2016/0334477 A1    Nov. 17, 2016

(51) Int. Cl.
*G01V 3/00* (2006.01)
*G01R 33/28* (2006.01)
*G01R 33/31* (2006.01)
*G01R 33/48* (2006.01)
*A61N 1/40* (2006.01)
*G01R 33/3415* (2006.01)

(52) U.S. Cl.
CPC ........... *G01R 33/288* (2013.01); *A61N 1/403* (2013.01); *G01R 33/31* (2013.01); *G01R 33/4804* (2013.01); *G01R 33/3415* (2013.01)

(58) Field of Classification Search
CPC .. G01R 33/288; G01R 33/31; G01R 33/4804; A61N 1/403
See application file for complete search history.

(56) References Cited

U.S. PATENT DOCUMENTS

| | | | |
|---|---|---|---|
| 7,336,074 B2 | 2/2008 | Yang et al. | |
| 2010/0145420 A1* | 6/2010 | Zhu ........................ | A61B 5/055 607/103 |
| 2013/0123885 A1* | 5/2013 | Zhu ........................ | A61B 18/12 607/100 |
| 2013/0147475 A1* | 6/2013 | Yang ................ | G01R 33/34046 324/309 |
| 2015/0273230 A1* | 10/2015 | Guerin .................. | A61N 1/403 607/101 |

* cited by examiner

*Primary Examiner* — Daniel Miller
(74) *Attorney, Agent, or Firm* — Beyer Law Group LLP

(57) ABSTRACT

A method for providing SAR focusing at a target in a body using an MRI system is provided. A computed pulse is provided at a lower power to the body. A MR thermometry is performed. A map is created from the MR thermometry to determine if a hotspot aligns with the target. If the target does not align with the hotspot, then the steps are performed comprising, recomputing the computed pulse, providing the computed pulse at a lower power to the body, performing MR thermometry, creating a map from the MR thermometry to determine if a hotspot aligns with the target, and repeating these steps until the hotspot aligns with the target. The computed pulse is applied at a higher power to the body to provide the desired SAR at the target. Temperature change is monitored with MR thermometry the previous two steps are repeated until desired temperature is achieved.

12 Claims, 7 Drawing Sheets

METHOD AND APPARATUS FOR SAR FOCUSING WITH AN ARRAY OF RF TRANSMITTERS

GOVERNMENT RIGHTS

This invention was made with Government support under contract EB015891 awarded by the National Institutes of Health. The Government has certain rights in the invention.

BACKGROUND OF THE INVENTION

This application relates generally to the creation of local hyperthermia, or specific absorption ratio focusing, using an array of radio frequency transmitters.

SUMMARY OF THE INVENTION

In accordance with the invention, an efficient algorithm for determining the optimal channel weightings of an array of transmitters to achieve specific absorption rate (SAR) focusing is provided. This algorithm is particularly useful when used in conjunction with magnetic resonance imaging (MRI) to provide real-time temperature mapping, to monitor and refine the focusing of the computed pulse as follows: A computed pulse is provided at a lower power from the transmit array to the body. MR thermometry is performed using the MRI system. A map is created from the MR thermometry to determine if a hotspot aligns with the target. If the target does not align with the hotspot, then the steps are performed comprising, recomputing the computed pulse, providing the computed pulse at a lower power from the MRI system to the body, performing MR thermometry using the MRI system, creating a map from the MR thermometry to determine if a hotspot aligns with the target, and repeating these steps until the hotspot aligns with the target. The computed pulse is applied at a higher power to the body to achieve the desired therapeutic effect. Temperature change is monitored with MR thermometry. The previous two steps are repeated until desired temperature is achieved.

In another manifestation of the invention, an apparatus for achieving SAR focusing at a target in a body is provided. The apparatus comprises a plurality of transmission coils, at least one static magnetic field coil, at least one gradient coil, a plurality of receiving coils, and a controller electrically connected to the plurality of transmission coils, the at least one static magnetic coil, the at least one gradient coil, and the plurality of receiving coils. The controller comprises a processor and computer readable media. The computer readable media comprises computer readable code for providing a computed pulse at a lower power from the MRI system to the body, computer readable code for performing MR thermometry using the MRI system, computer readable code for creating a map from the MR thermometry to determine if a hotspot aligns with the target, wherein if the target does not align with the hotspot the computer readable code perform the steps comprising recomputing the computed pulse, providing the computed pulse at the lower power from the MRI system to the body, performing MR thermometry using the MRI system, creating a map from the MR thermometry to determine if a hotspot aligns with the target, and repeating these steps until the hotspot is sufficiently aligned with the target, computer readable code for applying the computed pulse at a higher power to the body to provide SAR focusing at the target; computer readable code for monitoring temperature change with MR thermometry. Another significant aspect of the apparatus involves the computational software for electromagnetic modeling and optimization, including the library of numerical coil and body models that are used to estimate the electric-fields that are needed determine the optimal pulse.

In another manifestation of the invention, a method for providing specific absorption rate (SAR) focusing to target voxels in a body with the target voxels and with non-target voxels surrounded by a plurality of transmission coils is provided. A computed pulse is determined comprising solving a constrained optimization problem for maximizing SAR averaged over the target voxels while constraining the peak local SAR over the non-target voxels, wherein the optimization problem is solved using an interior-point method that approximates the constraints with a log-barrier function, wherein derivatives (gradients and Hessians) supplied to the interior-point algorithm are computed efficiently using a vectorized SAR oracle. The computed pulse is applied to the body to provide SAR focusing to the target using the plurality of transmission coils.

The invention and objects and features thereof will be more readily apparent from the following detailed description and appended claims when taken with the drawings.

DETAILED DESCRIPTION OF ILLUSTRATED EMBODIMENTS

Figure 1:
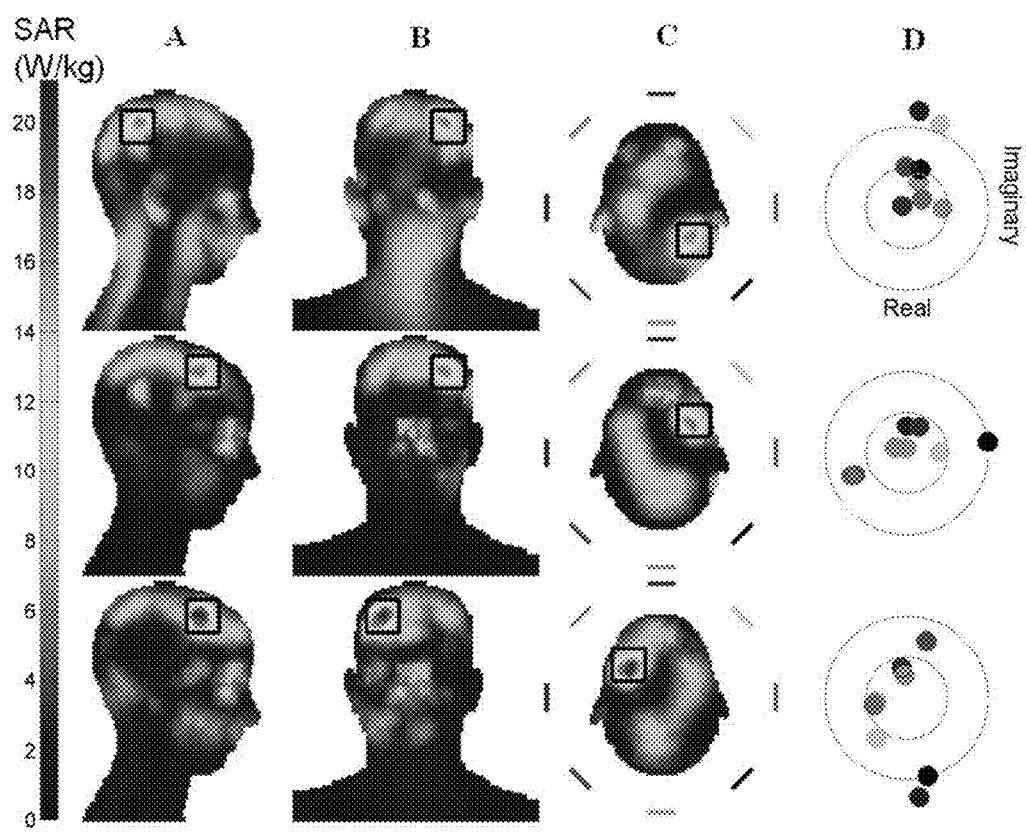
FIG. 1 shows maximum intensity projections of optimized local SAR distributions.

The present invention will now be described in detail with reference to a few preferred embodiments thereof as illustrated in the accompanying drawings. In the following description, numerous specific details are set forth in order to provide a thorough understanding of the present invention. It will be apparent, however, to one skilled in the art, that the present invention may be practiced without some or all of these specific details. In other instances, well known process steps and/or structures have not been described in detail in order to not unnecessarily obscure the present invention.

To give motivation for the invention, there are several possible applications and mechanisms through which SAR focusing could achieve therapeutic effect. One possibility involves targeted hyperthermia (heating of a specific region of anatomy to a temperature of 41-45° C.). Hyperthermia can have applications in cancer treatment where the cytotoxicity of x-rays has been shown to be greater at elevated temperatures thus allowing focused heating to be an effective way to improve the efficiency and spatial selectivity of radiation therapy. Certain forms of chemotherapy have also been shown to be more potent at higher temperatures probably due increased rate of chemical processes at greater temperatures. Furthermore, it is possible to enclose the drugs in thermosensitive liposomes whose membranes are permeable only above a certain temperature, thus allowing for localized drug delivery through hyperthermia.

Another potential application of the SAR focusing concept is neuromodulation whereby rapid deposition of energy can alter neuronal activity. While the mechanism of neuromodulation is still not well understood, the proposed method could be an effective means for achieving MR-guided focal neuromodulation and would be of particular value to cognitive neuroscience researchers and for risk-free neurostimulation in healthy patients and subjects.

An embodiment of the invention provides a procedure for achieving SAR focusing within the bore of an MRI scanner. The apparatus consists of an RF applicator with multiple independently controlled transmitters operating at a sufficiently high frequency to produce local hotspots that are both electronically steerable and small enough to have therapeutic value. The method is not restricted to a particularly design choice for the individual transmitters so long as the array allows for independent control of magnitude and phase of the amplitude of the transmitter's waveform. The applicator could be a separate array consisting of transmitters operating at much higher frequency than the MR Larmor frequency or could be the same multichannel transmit coil array used for parallel transmission if the MR static field strength is sufficiently high and the number and size/position of the transmit array elements is sufficient. Temperature mapping will be performed using one of many well-developed MR thermometry sequences. These include methods using the temperature dependence of T1 or T2 relaxation times, the proton resonance frequency chemical shift, or the change in the diffusion constant with temperature. With the described multichannel array, the location of a hotspot during application of an RF pulse will vary depending on the amplitudes and phases that are applied to each channel, thus allowing for electronic control of hotspot locations. A crucial component of the procedure is a rigorous pulse design method that accounts for interpatient anatomical variations and is able to incorporate thermometry feedback in real time due to the efficiency of the optimization algorithm used for pulse design. A more complete embodiment of the SAR focusing under MR guidance will now be described in detail and is depicted in FIG. 7.

Figure 7:
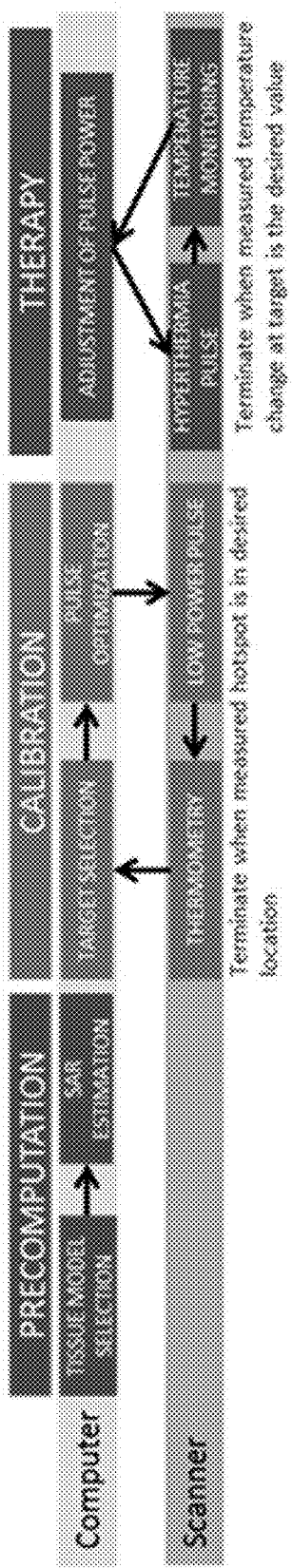
FIG. 7 illustrates a method used in an embodiment.

FIG. 7 illustrates a method used in an embodiment. First, an anatomical image must be obtained for the purpose of both identifying the abnormality to establish the target location and providing information about the patient's electrical properties for electric field estimation and subsequent pulse optimization. As electric fields are difficult to estimate through measurement, they would likely be obtained through an electromagnetic simulation using a realistic transmit array element model and a tissue model chosen to closely match the patient. For applications with a large target size and patients without significant tissue abnormalities, it may be sufficient to find a closely matched body model from a library and use electric fields that have been precomputed on the members of this library. For more demanding applications or patients with abnormal tissue properties, it may be necessary to create a custom tissue model through segmentation of the anatomical image and perform the numerical simulation in real-time. In this case, there can be significant computation time (from several minutes to an hour) between anatomical imaging and the actual procedure and it may be better to perform imaging at a prior scan session and have computation happen offline. In addition to reducing the amount of time the scanner is idle, this would have the benefit of allowing the anatomical imaging to be performed at a lower field strength which would eliminate the B1+ inhomogeneity issues that are present at higher fields and would result in a more reliable segmentation and subsequent electric field estimation. Using either of the above workflows, an anatomical image and a set of electric field maps for each transmit channel will be obtained prior to the procedure.

The procedure begins with the target location being selected through analysis of the anatomical image. This location corresponds to certain voxels on the grid used for electric field estimation. Determining the optimum pulse (amplitude and phase of transmitted wave to be applied to each channel of the transmit array) for the particular target involves a rigorous numerical optimization. It is necessary to maximize the mean value of the SAR over all target voxels while still satisfying all other constraints typically imposed during imaging. These constraints include keeping the local SAR in healthy tissue, global SAR over entire exposed mass, and average power at each transmit channel below some predefined limit. This "maxSAR" optimization problem can be stated as follows:

MINIMIZE: $SAR(b) = \max_{r=1,\ldots,N_R}(b^H R_r b)$

SUBJECT TO: $SAR_{target}(b) = b^H Q_{target} b \geq 1$

The variable b is a vector that denotes the complex amplitudes to be applied to each transmit channel. The SAR spatially averaged over a volume V can be found from the single channel electric field maps and the model's tissue properties as $$SAR_V = \frac{1}{V}\int_V \frac{\sigma(r)\|E(r)\cdot b\|_2^2}{2\rho(r)} dV$$

Here $\|E(r)\cdot b\|_2^2$ represents the magnitude of the total electric field vector at position r found through summation of the single channel vectors weighted by the channel amplitudes. The resulting power deposition is found by incorporating the conductivity of the tissue at that location $\sigma(r)$. The voxelwise SAR at r is then found by normalizing by the mass density $\rho(r)$. Spatially averaging is then performed over the volume of interest. For evaluating the 10 g spatially averaged local SAR at a particular voxel, V corresponds to a 10 g cubical mass surrounding that voxel. Local SAR at all healthy tissue voxels must be below the regulatory limit (e.g. 10 W/kg for head) during the procedure. Global SAR, where V corresponds to the entire exposed mass, must also be kept below a regulatory limit (e.g. 3.2 W/kg for head). Finally, average power at each transmit channel must be kept below the hardware limit. With some manipulation, all three quantities can be expressed in the form $b^H R b$ where R is a positive semidefinite symmetric matrix. For the SAR terms, R incorporates conductivity, mass density and electric field maps and for the power term, R is a zero matrix except for the diagonal entry corresponding to a particular channel. For a coil with $N_c$ channels and a tissue grid with $N_v$ voxels the total number of constraints is $N_R = N_v + 1 + N_c$. If each R matrix is normalized by the value of the corresponding absolute regulatory limit for the constraint, the expression $SAR(b) = \max_{r=1,\ldots,N_R}(b^H R_r b)$ serves as a normalized cost function that must be minimized. If SAR(b)≤1 then all constraints are satisfied and if SAR(b)>1 some constraint is violated. We wish to minimize SAR(b) subject to the constraint that the SAR spatially averaged over the target volume is greater than 1. The SAR at the target can be expressed as $b^H Q_{target} b$ where $Q_{target}$ is found as described for local and global SAR with V corresponding to the voxels in the target. Once the optimal pulse vector b is found its amplitude can be scaled by a factor of SAR(b) so that the regulatory limits are met exactly, thus allowing for SAR at the target to be maximized without violating any safety or hardware constraints.

The maxSAR constrained optimization is nonconvex and can be solved using an interior point algorithm that relies on converting the problem into an unconstrained minimization by approximating the constraint by a continuous log barrier function that approaches zero when the constraint is satisfied and approaches infinity when the constraint is violated. At each iteration of this algorithm, a descent direction is found based on the values of $SAR_{target}$ and SAR as well as both of their gradients and Hessians. Using this method, the optimization problem can be solved in 10-20 seconds for a particular target location. Despite being a nonconvex problem, just 5 initial conditions were found to be sufficient to reliably generate a satisfactory pulse. As seen in FIG. 1, for three arbitrarily chosen target locations, it is possible to find a pulse that generates a hotspot in the target while keeping SAR at all remaining voxels below 10 W/kg (the regulatory limit for local SAR). The computation times and maximum SAR in the target region are given in Table 1:

TABLE 1

Optimization results for three target regions.

| Target | Computation time (s) | Maximum SAR (W/kg) |
|---|---|---|
| 1 | 9.34 | 16.5 |
| 2 | 10.15 | 16.1 |
| 3 | 11.94 | 21.3 |

Figure 2:
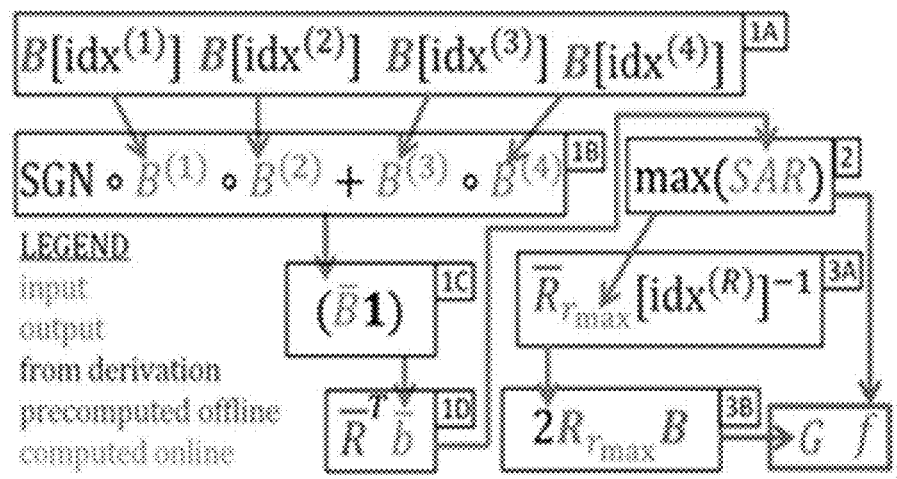
FIG. 2 shows a general procedure used in an embodiment of the invention.

Typically $N_v$ is quite large (>$10^5$) thus making this computation at each iteration quite costly and making the duration of the optimization several hours. However, it can be shown that computation time can be decreased significantly (to the values shown in Table 1) through a vectorized SAR oracle by manipulating the expression SAR(b) in a way that can be evaluated efficiently. A description of this vectorized oracle is shown in FIG. 2. In FIG. 1 maximum intensity projections of optimized local SAR distributions for three different 4 cm³ targets are shown as black squares showing in column A sagital views, column B coronal views, and column C axial views. Column D shows the optimal complex channel weighting with loop locations in (C).

A more detailed description of the vectorized SAR oracle which makes this fast maxSAR optimization is now provided. A transmit pulse train of duration T whose complete RF waveform is parameterized by $N_c N$ complex variables corresponding to the complex amplitudes applied to each of $N_c$ transmit channels at each of N subpulses at different excitation k-space locations throughout the scan. These variables can be characterized by a matrix $B \in \mathbb{C}^{N_c \times N}$ whose nth column denoted $b_n$ represents the channel amplitude at the nth subpulse. It has been shown that local SAR, global SAR, and average power for a given channel weighting can all be expressed as positive semidefinite (PSD) quadratic forms $b_n^H R_r b_n$ where $R_r$ is either a local SAR matrix at one of $N_v$ voxels, a global SAR matrix for the entire exposed mass, or an average power matrix at one of $N_c$ channels. If each $R_r$ includes a normalization by the regulatory limit for the corresponding quantity as well as the duration of the scan (T), the expression $f(B) = \max_{r=1,\ldots,N_R}(SAR)$, where the vector SAR is defined as $SAR_r = \sum_{n=1}^{N} b_n^H R_r b_n$, serves as a time-averaged cost function for all $N_R = N_v + N_c + 1 \approx N_v$ safety/hardware constraints. Because of the normalization, when f>1, some regulatory limit is violated. Pulse design problems can be formulated to minimize f subject to some constraint on excitation accuracy. The optimal value of f then represents the amount by which the RF duty cycle can be scaled to abide by regulatory limits. To perform such an optimization it is necessary to repeatedly evaluate not only f but also its gradient (or more correctly its subgradient since f is nondifferentiable). The subgradient for a particular $b_n$ is denoted by the vector $g_n \in \mathbb{C}^{N_c}$ and the matrix G is defined as $[g_1 \ldots g_N]$. An efficient oracle is desired that receives B and outputs f and G in the minimum amount of time. The general procedure is illustrated in FIG. 2. To do this procedure is (1) compute SAR from B, (2) compute f and $r_{max}$ from SAR, where $f = \max(SAR) = SAR_{r_{max}}$, (3) compute a subgradient through analytical differentiation of the cost function at the peak voxel: $G = 2R_{r_{max}} B$. Among these steps, (1) is the most costly and extremely slow if done inefficiently in a loop over r and n. This step can be made vastly more efficient by exploiting the symmetry of $R_r$ to evaluate the quadratic form $b_n^H R_r b_n$ in a vectorized manner. It can be shown that the entire vector SAR can be obtained through a single matrix vector multiplication $\overline{R}^T \overline{b}$ as in (1 A-D) in FIG. 2. The first step (1A) consists of creating new real-valued matrices $B^{(\cdot)} \in \mathbb{R}^{N_c^2 \times N}$ whose se nth column consists of the real and imaginary components of $b_n$ at indices $idx^{(\cdot)}$ (whose identity can be derived). Next, $\overline{b}$ is found by first forming $\overline{B}$ through elementwise operations on a matrix SGN (whose identity can be derived) and $B^{(\cdot)}$ (1B) then time-averaging the columns of $\overline{B}$ (1C). SAR is found through a dense matrix vector multiplication $\overline{R}^T \overline{b}$ (1D) where the rth column of $\overline{R} \in \mathbb{R}^{N_c^2 \times N_R}$ is found by selection of the $N_c^2$ unique components of the PSD SAR matrix $R_r$ at indices $idx^{(R)}$. In fact, $\overline{R}$ can be precomputed directly from electric fields and tissue properties, entirely bypassing construction of SAR matrices. The single SAR matrix $R_{r_{max}}$, which is the Hessian of f, can be reconstructed from $\overline{R}_{r_{max}}$, the $r_{max}$th column of $\overline{R}$ (3A) and used in subgradient computation (3B).

Figure 3:
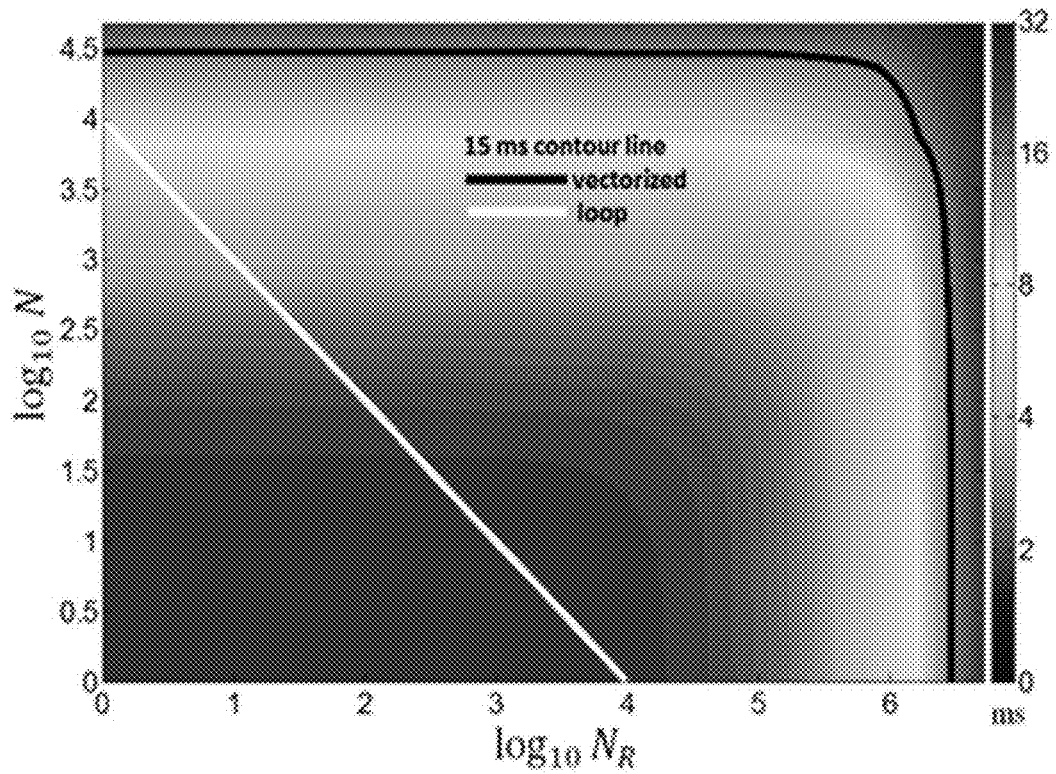
FIG. 3 is a graph of computation time for a vectorized oracle

FIG. 3 is a graph of computation time for a vectorized oracle, and shows computation time scales with $N_R N$ when using a loop; therefore, even with just one subpulse (N=1), the maximum possible value of $N_R$ is $10^4$ which is an order of magnitude less than the number of voxels in a body model. Using the vectorized method, computation time is approximately constant regardless of N or $N_R$. Oracle computation time is within an acceptable range for $N \le 10^4$ and $N_R \le 10^6$. The implication of this is that the maxSAR algorithm can be applied to body models with up to $10^6$ voxels without any precompression. This is especially important for higher frequencies of transmission when the size of the simulation grid becomes finer and this scalability of the vectorized SAR oracle becomes particularly important.

The speed of this optimization algorithm allows for an iterative pulse calibration procedure using thermometry feedback. To begin, the anatomical image will be analyzed to determine the location of the abnormality and define this target on the body model. The maxSAR optimization problem can then be solved with this target to determine some optimum pulse. However, due to patient-body model mismatch, this pulse may not be truly optimal and may produce a hotspot in a location that is not exactly aligned with the desired target. To address this problem the pulse will first be applied at a power level that is low enough to not have a physiological effect but high enough to produce enough heating that can be measured through MR thermometry. By applying a thermometry sequence following the heating pulse, and then aligning this temperature map with the anatomical image, the location of the hotspot can be determined. By determining the offset of the true hotspot location from the desired location, the target region on the body model can be refined and the optimization can be performed with the new target. This can be done iteratively until the measured hotspot is in the desired location. Unlike some other hyperthermia methods, redoing the pulse design with a new target does not consist of performing repeated time-consuming electromagnetic simulations. Once the single-channel electric field maps have been estimated, the vectorized SAR oracle can be constructed and used to perform repeated optimizations efficiently.

Once the truly optimal pulse has been found through the above calibration process, the actual procedure can be performed using a pulse with the same channel amplitude but with a power level that is as high as possible while still satisfying SAR(b)≤1. The pulse sequence will consist of a train of RF pulses with very short repetition time. This pulse train will be applied continuously until SAR(b), as estimated based on the scanner's measured value of global SAR and the ratio of local SAR to global SAR as determined in simulation, reaches a certain value. Then the temperature mapping sequence will be applied to determine the actual change in temperature at all regions including both the target and surrounding tissue. In the first embodiment where the RF applicator is separate from the imaging coil, temperature mapping can be performed continuously, at the same time as the heating. In the second embodiment, temperature mapping will be interleaved with the heating pulse using the same transmit array. This sequence will be as fast as possible to minimize cooling during the temperature measurement. Following temperature mapping, an additional RF pulse train will be applied if the temperature at the target has not reached the desired range. These interleaved heating and thermometry sequences will be repeated until the target temperature is reached.

Figure 4:
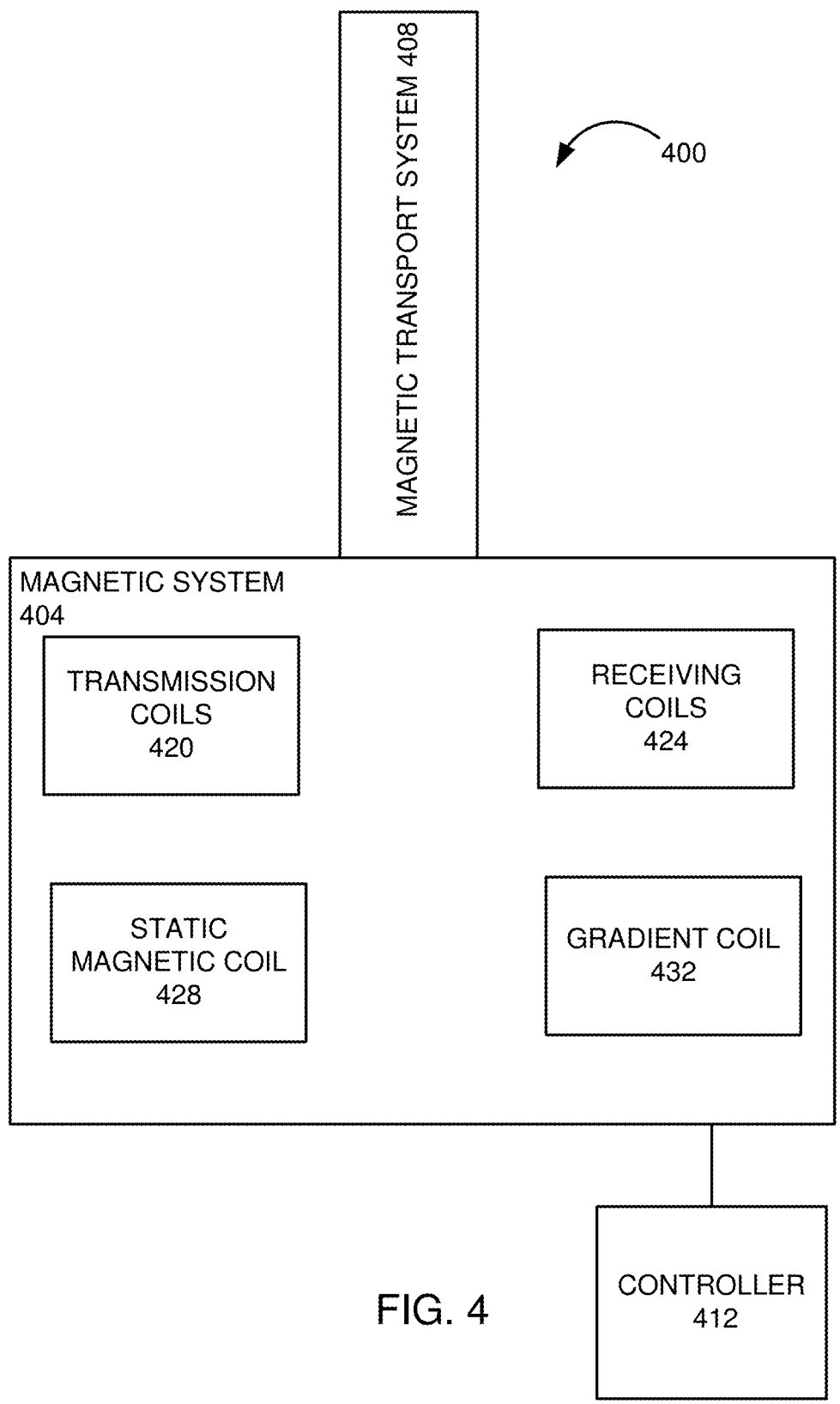
FIG. 4 is a schematic top view of a magnetic resonance imaging (MRI) system that may be used in an embodiment of the invention.

To further facilitate understanding of the invention, FIG. 4 is a schematic top view of a MRI system 400 that is adapted to provide SAR focusing in an embodiment of the invention. The MRI system 400 comprises a magnet system 404, a patient transport or support table 408 connected to the magnet system 404, and a controller 412 controllably connected to the magnet system. In this embodiment, the magnet system 404 comprises a plurality of transmission coils 420, a plurality of receiving coils 424, at least one static magnetic coil 428, and at least one gradient coil 432. In one example, a patient (subject) would lie on the patient transport table 408 and the magnet system 404 would pass around the patient. The controller 412 would control magnetic fields and radio frequency (RF) signals provided by the transmission coils and would receive signals from the receiving coils 424, while the static magnetic coil provides static magnetic field and the gradient coil 432 creates a gradient field in the magnet system 404.

Figures 8A, 8B:
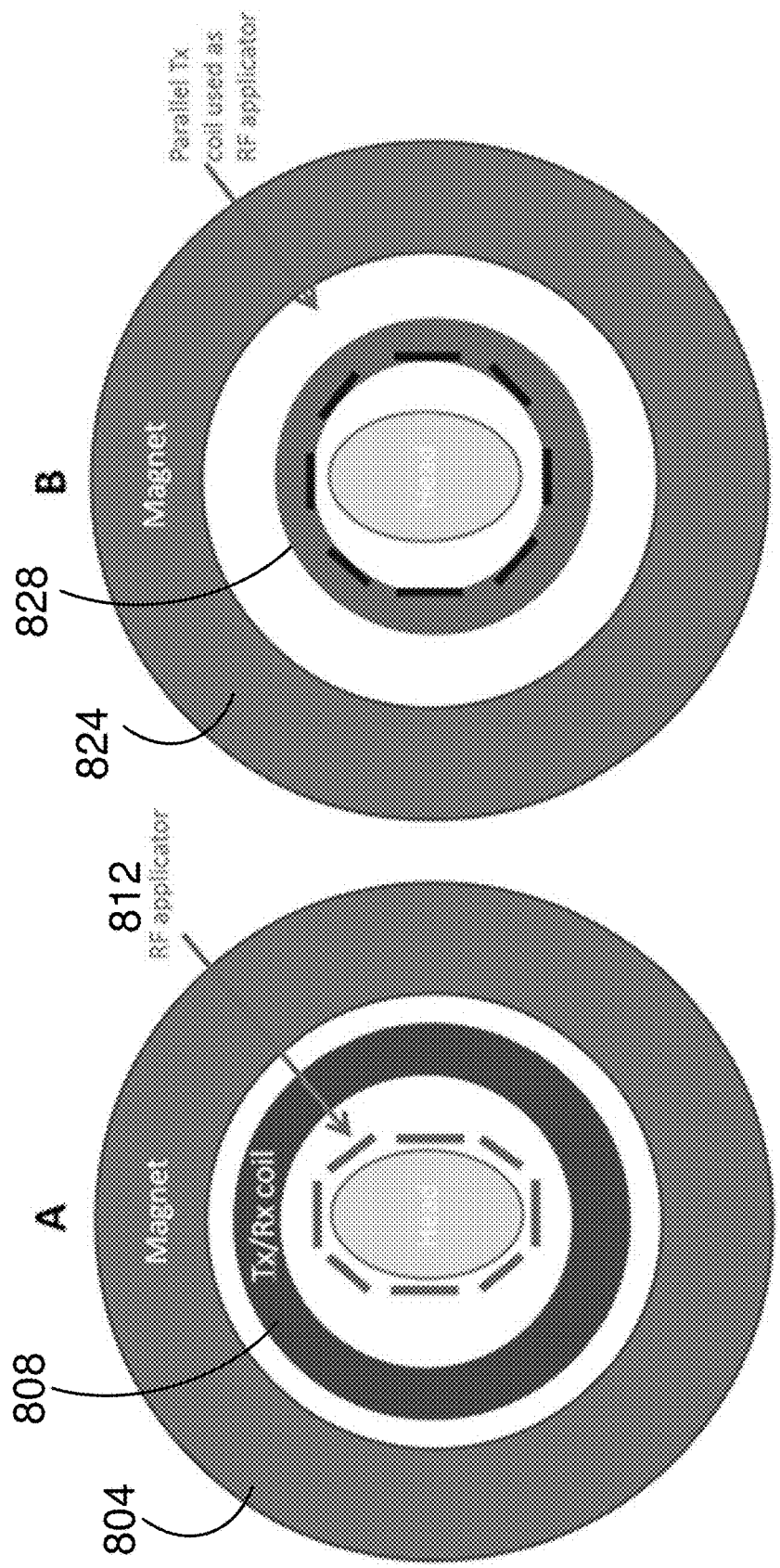
FIG. 8A illustrates a magnetic system with a first configuration that is used in an embodiment.
FIG. 8B illustrates a magnetic system with a second configuration that is used in another embodiment.

FIG. 8A illustrates a magnetic system with a first configuration that is used in an embodiment. In this embodiment the static magnetic coil and gradient coil are provided by the magnet 804, which may comprise a plurality of coils. The transmission coils and receiving coils are provided by the Tx/Rx coil 808, which may comprise a plurality of coils. A separate RF array applicator 812 is placed around the subject and is separate from the Tx/Rx coil 808 used for imaging.

FIG. 8B illustrates a magnetic system with a second configuration that is used in another embodiment. In this embodiment the static magnetic coil and gradient coil are provided by the magnet 824, which may comprise a plurality of coils. The transmission coils and receiving coils are provided by the Tx/Rx coil 828, which may comprise a plurality of coils. In this configuration the Tx/Rx coil 828 used for imaging is also used as the RF applicator for SAR focusing.

Figure 5:
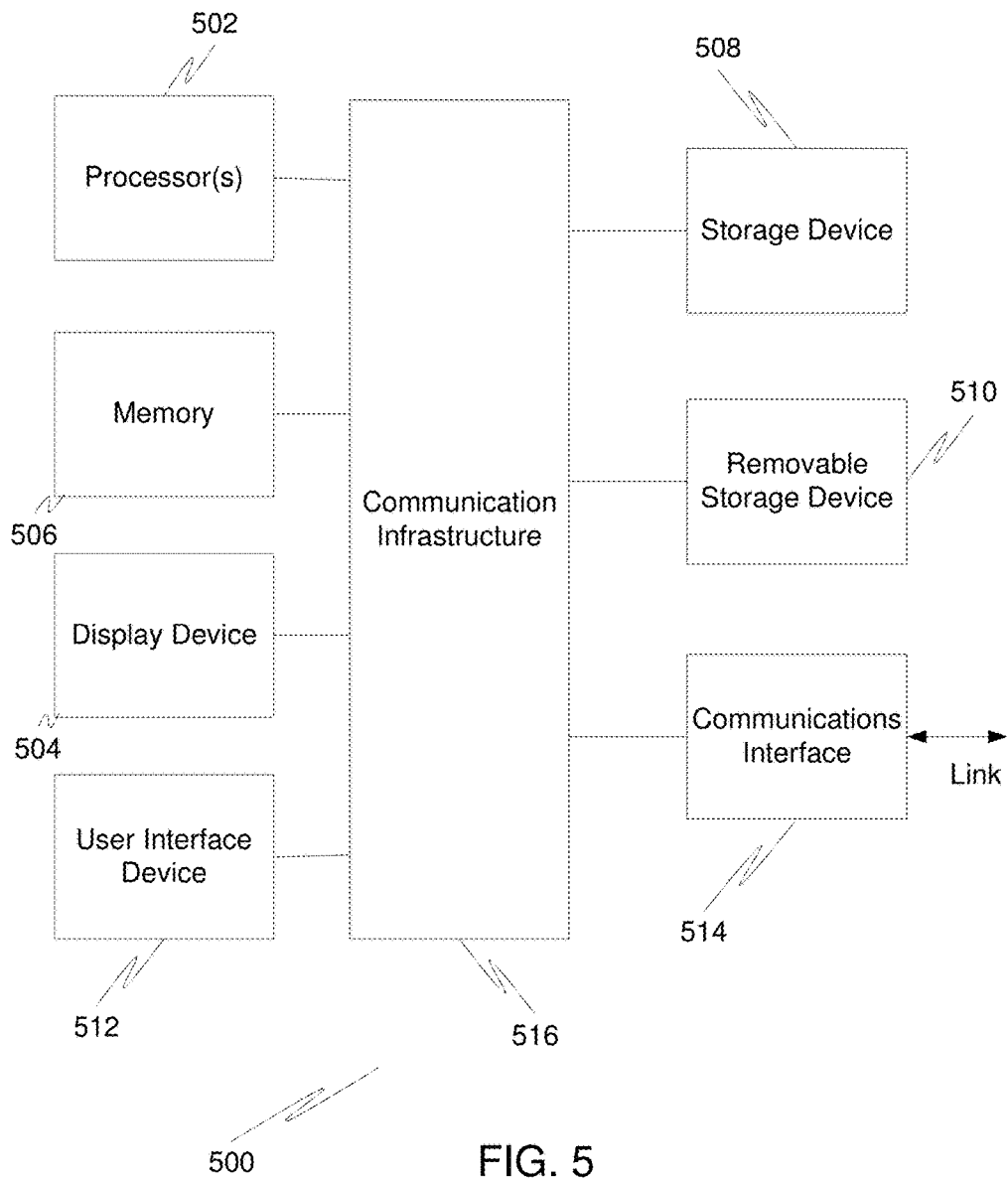
FIG. 5 is a high level block diagram showing a computer system.

FIG. 5 is a high level block diagram showing a computer system 500, which is suitable for implementing the controller 412 used in embodiments of the present invention. The computer system may have many physical forms ranging from an integrated circuit, a printed circuit board, and a small handheld device up to a super computer. The computer system 500 includes one or more processors 502, and further can include an electronic display device 504 (for displaying graphics, text, and other data), a main memory 506 (e.g., random access memory (RAM)), storage device 508 (e.g., hard disk drive), removable storage device 510 (e.g., optical disk drive), user interface devices 512 (e.g., keyboards, touch screens, keypads, mice or other pointing devices, etc.), and a communication interface 514 (e.g., wireless network interface). The communication interface 514 allows software and data to be transferred between the computer system 500 and external devices via a link. The system may also include a communications infrastructure 516 (e.g., a communications bus, cross-over bar, or network) to which the aforementioned devices/modules are connected.

Information transferred via communications interface 514 may be in the form of signals such as electronic, electromagnetic, optical, or other signals capable of being received by communications interface 514, via a communication link that carries signals and may be implemented using wire or cable, fiber optics, a phone line, a cellular phone link, a radio frequency link, and/or other communication channels. With such a communications interface, it is contemplated that the one or more processors 502 might receive information from a network, or might output information to the network in the course of performing the above-described method steps. Furthermore, method embodiments of the present invention may execute solely upon the processors or may execute over a network such as the Internet in conjunction with remote processors that shares a portion of the processing.

The term "non-transient computer readable medium" is used generally to refer to media such as main memory, secondary memory, removable storage, and storage devices, such as hard disks, flash memory, disk drive memory, CD-ROM and other forms of persistent memory and shall not be construed to cover transitory subject matter, such as carrier waves or signals. Examples of computer code include machine code, such as produced by a compiler, and files containing higher level code that are executed by a computer using an interpreter. Computer readable media may also be computer code transmitted by a computer data signal embodied in a carrier wave and representing a sequence of instructions that are executable by a processor.

Figure 6:
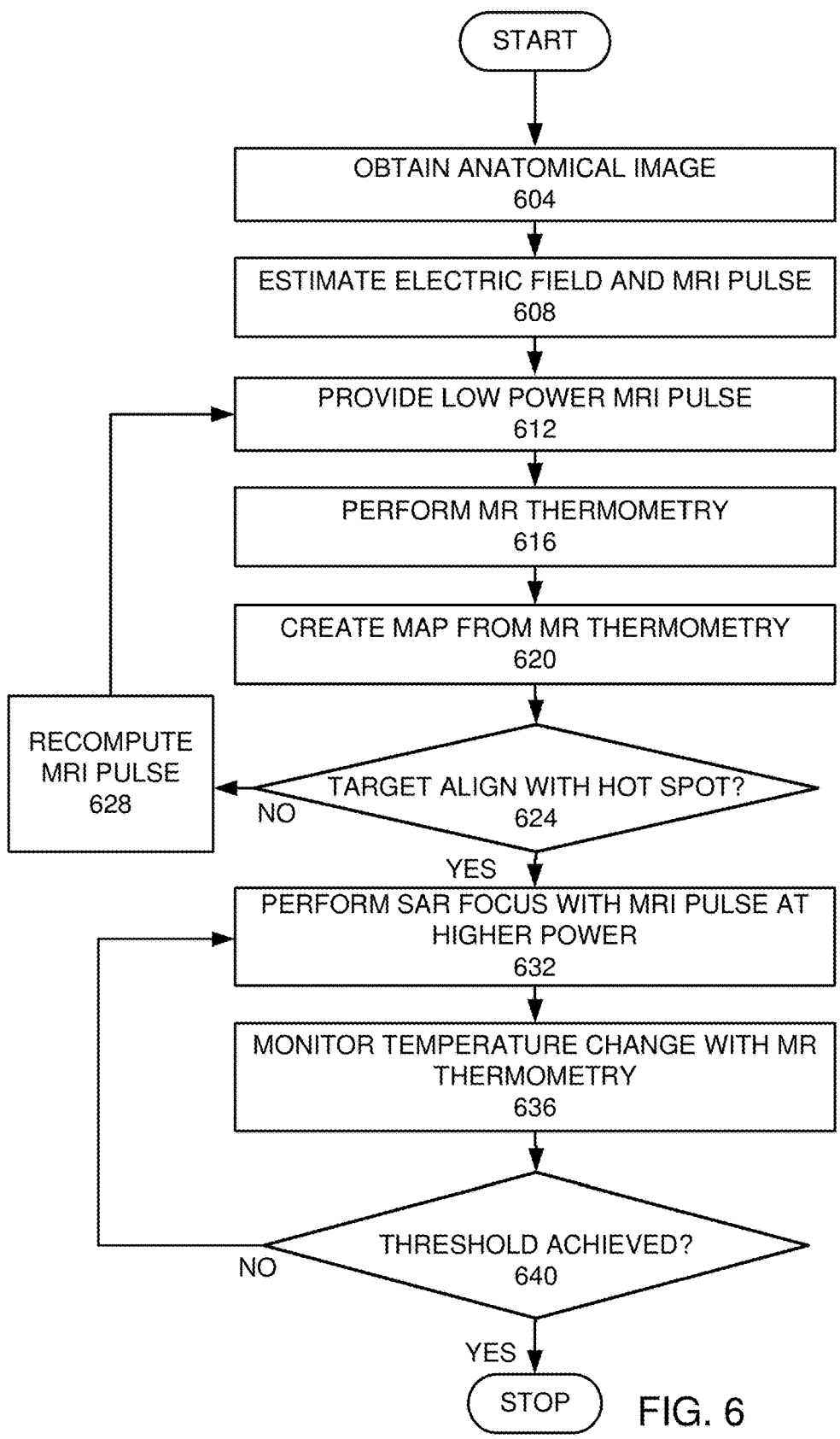
FIG. 6 is a flow chart of a process used in an embodiment of the invention.

FIG. 6 is a flow chart of a process used in an embodiment of the invention. A subject is placed in the MRI system 400. An anatomical image is made of at least part of the subject (step 604). MRI may be used to generate the anatomical image in an embodiment of the invention. The anatomical image is used to determine a location of a target hotspot. An estimation of electric fields forming a body model of electrical properties is provided (step 608). The estimation is used to provide a computed MRI pulse. A low power computed MRI pulse is provided by the magnet system 404 (step 612). MR thermometry is performed using the MRI system 400 (step 616). A map is created from the MR thermometry (step 620). A comparison is made to see if the hotspot of the map is aligned with the target hotspot (step 624). If the target hotspot does not align with the hotspot of the map, then the MRI pulse is recomputed (step 628), and the process returns back to step 612, where the low power computed MRI pulse is the recomputed MRI pulse (step 612). This process of steps 612 to 628 is repeated until the target hotspot is sufficiently aligned with the hotspot of the map.

After the target hotspot is sufficiently aligned with the hotspot of the map, a SAR focusing is performed at a higher power using the recomputed MRI pulse to achieve the desired effect at the target (step 632). The temperature is measured using MR thermometry (step 636). A determination is made whether the desired effect has been reached (step 640). Such a determination may be whether the target has been heated to a target temperature for a target time. Such a determination may be made by determining if a threshold temperature has been achieved for a threshold time. If the SAR focusing is not complete, then the process returns to step 632, performing therapy with the recomputed MRI pulse at the higher power. The process is repeated until the desired temperature is reached.

In an embodiment, MRI may be used to estimate electric fields forming a body model. In another embodiment, a tissue model may be used to estimate electric fields forming a body model. In an embodiment, the anatomical image is obtained and the electric field is estimated before the subject is placed on the MRI system 400. In an embodiment, the independently controlled transmission coils are operated at a high enough frequency to create electronically steerable hotspots. In an embodiment, it is preferred to have at least 8 transmission coils. Preferably the operating frequency of the MRI system is between 30 MHz to 10 GHz. More preferably, the operating frequency of the MRI system is between 100 MHz to 3 GHz. Most preferably, the operating frequency of the MRI system is between 300 MHz and 1 GHz.

Some embodiments, as described above, provide a fast calculation of the computed pulse. If the calculation of the pulse takes a long time, for example over 30 minutes, a thermal therapy using MR would be too slow and undesirable. This is the case with many existing methods of hyperthermia pulse calculation such as the time-reversal focusing method. The speed enabled by the maxSAR algorithm allows for a closed-loop iterative pulse optimization using thermometry feedback, thus allowing for increased robustness to patient/body model mismatch.

In embodiments, a higher power pulse is applied at high enough power that the SAR focusing results in achieve therapeutic effect at the target. A lower power pulse has less energy than the higher power pulse, and does not provide enough energy to have therapeutic effect at the target, but enough energy to allow identification of the hotspot and its spatial relationship to the target using MR thermometry. The lower power pulse would satisfy the local SAR constraints at all voxels including the target and thus would achieve a maximum of 10 W/kg local SAR. The amplitude of the pulse would be calculated so that the peak local SAR over the duration of the (continuously applied) pulse is under 10 W/kg. This low power pulse is applied until a detectable temperature change is obtained. The temperature at the target will rise to no more than 41 degree Celsius (and probably much lower). For the high power pulse, the maximum local SAR limit (e.g. of 10 W/kg) only applies to voxels outside the target. The peak power of the pulse would be greater than that of the lower pulse and may likely be at the amplifier limit (typically 6 kW). This pulse is applied until the desired therapeutic temperature is achieved at the target.

In an embodiment, the lower power pulse does not heat any part of the body to a temperature above 41° C. and the higher power pulse heats at least one part of the body to a temperature above 41° C. The desired temperature change is application specific and the invention is applicable to any desired level of temperature increase. This would only require modifying the duration and/or power at which the pulse is applied. Preferably the thermometry uses a lower power, which does not increase the temperature in any part of the body greater than 1° C. The SAR focusing uses a higher power, which increases the temperature of part of the body at least 3° C. SAR focusing may have therapeutic, diagnostic, and research uses. Therapeutic uses include thermal therapy, such as hyperthermia. A threshold temperature for a threshold time would be the temperature and time needed to complete the thermal therapy. Research uses include neuromodulation.

While this invention has been described in terms of several preferred embodiments, there are alterations, permutations, modifications and various substitute equivalents, which fall within the scope of this invention. It should also be noted that there are many alternative ways of implementing the methods and apparatuses of the present invention. It is therefore intended that the following appended claims be interpreted as including all such alterations, permutations, modifications, and various substitute equivalents as fall within the true spirit and scope of the present invention.

What is claimed is:

1. A method for providing specific absorption rate (SAR) focusing to a target area in a body of a subject using a magnetic resonance imaging (MRI) system with a plurality of transmission coils, comprising:
   a) maximizing local SAR within a target region while constraining a peak SAR outside the target to be below a safety limit;
   b) formulating a problem as a constrained optimization to find optimal transmission coil weights without specifying an optimal field distribution;
   c) using a vectorized SAR oracle to calculate a value and gradient of all SAR and power terms including all local SAR, global SAR, and average power terms for a given transmission coil weighting;
   d) obtaining an electric field distribution generated by each transmission coil within the body of the subject in a subject-specific way;
   e) providing a computed pulse at a lower power from the MRI system to the body;
   f) performing MR thermometry using the MRI system;
   g) creating a map from the MR thermometry to determine if a hotspot aligns with the target;
   h) if the target does not align with the hotspot, performing the steps comprising:
      recomputing the computed pulse;
      providing the computed pulse at the lower power from the MRI system to the body;
      performing MR thermometry using the MRI system;
      creating a map from the MR thermometry to determine if a hotspot aligns with the target; and
      repeating this step h until the hotspot aligns with the target;

i) applying the computed pulse at a higher power to the body to provide SAR focusing to the target;

j) monitoring temperature change with MR thermometry; and k) repeating steps i and j until a threshold temperature for a threshold time at the target is achieved.

2. The method, as recited in claim 1, further comprising:
collecting an MR image of the body through the MRI system;
using the MR image to determine a location of the target;
using the MR image to create a body model of electrical properties;
using numerical simulations on the body model of electrical properties to determine subject specific electric fields or estimating SAR from a precomputed library of body models;
defining a target location;
using an interior point algorithm with the vectorized SAR oracle for function and gradient evaluation; and
computing computed pulse for providing a SAR focusing.

3. The method, as recited in claim 2, wherein the step i comprises using constructive interference of the computed pulse from the plurality of transmission coils to provide heating to the target area and destructive interference of the computed pulse from the plurality of transmission coils to reduce heating of the body away from the target area.

4. The method, as recited in claim 3, wherein step i further comprises maximizing a mean value of a SAR over the target hotspot, to be closest to a target temperature, while keeping a global SAR below a threshold and keeping power provided to non-target regions below a threshold.

5. The method, as recited in claim 1, wherein step i comprises using constructive interference of the computed pulse from the plurality of transmission coils to provide heating to the target area and destructive interference of the computed pulse from the plurality of transmission coils to reduce heating of the body away from the target area.

6. The method, as recited in claim 5, wherein step i further comprises maximizing a mean value of a SAR over the target hotspot, to be closest to a target temperature, while keeping a global SAR below a threshold and keeping power provided to non-target regions below a threshold.

7. The method, as recite in claim 1, wherein the monitoring temperature change with MR thermometry, comprises providing thermometry excitation sequences interleaved with the applying the computed pulse at the higher power to the body to provide thermal therapy to the target.

8. The method, as recited in claim 1, further comprising using a matched body model in a library to determine body specific electric fields.

9. An apparatus for providing specific absorption rate (SAR) focusing to a target area in a body of a subject, comprising:
a plurality of transmission coils of an MRI system, wherein during thermal therapy the transmission coils are located adjacent to the body;
at least one static magnetic field coil;
at least one gradient coil;
a plurality of receiving coils;
a controller electrically connected to the plurality of transmission coils, the at least one static magnetic coil, the at least one gradient coil, and the plurality of receiving coils, comprising:
a processor; and
non-transitory computer readable media storing computer-readable code that, when executed by the processor, causes the processor to:
formulate a problem as a constrained optimization to find optimal transmission coil weights without specifying an optimal field distribution;
use a vectorized SAR oracle to calculate a value and gradient of all SAR and power terms including all local SAR, global SAR, and average power terms for a given transmission coil weighting;
obtain an electric field distribution from each transmission coil in a subject-specific way;
provide a computed pulse at a lower power from the MRI system to the body;
perform MR thermometry using the MRI system;
create a map from the MR thermometry to determine if a hotspot aligns with the target;
determine when the target does not align with the hotspot, wherein when the target does not align with the hotspot the processor is cause to perform steps comprising:
recomputing the computed pulse;
providing the computed pulse at the lower power from the MRI system to the body;
performing MR thermometry using the MRI system;
creating a map from the MR thermometry to determine if a hotspot aligns with the target; and
repeating these steps until the hotspot is sufficiently aligned with the target;
apply the computed pulse at a higher power to the body to provide SAR focusing to the target; and
monitor temperature change with MR thermometry.

10. The apparatus, as recited in claim 9, wherein the non-transitory computer readable media further stores computer-readable code that, when executed by the processor, causes the processor to:
collect an MR image of the body through the MRI system;
use the MR image to determine a location of the target;
estimate SAR from a precomputed library of body models;
use the MR image to create a body model of electrical properties;
use numerical simulations on the body model of electrical properties to determine body specific electric fields;
define a target location;
use an interior point algorithm with the vectorized SAR oracle for function and gradient evaluation; and
compute a computed pulse for providing SAR focusing.

11. The apparatus, as recited in claim 10, wherein the computer readable code for applying the computed pulse at a higher power to the body to provide SAR focusing to the target comprises computer readable code for causing the processor to use constructive interference of the computed pulse from the plurality of transmission coils to provide heating to the target area and destructive interference of the computed pulse from the plurality of transmission coils to reduce heating of the body away from the target area.

12. The apparatus, as recited in claim 11, wherein the computer readable code for applying the computed pulse at a higher power to the body to provide SAR focusing to the target further comprises computer-readable code for causing the processor to maximize a mean value of a SAR over the target hotspot, to be closest to a target temperature, while keeping a global SAR below a threshold and keeping power provided to non-target regions below a threshold.

* * * * *